US00PP19569P2

(12) United States Plant Patent
Talmadge

(10) Patent No.: US PP19,569 P2
(45) Date of Patent: Dec. 9, 2008

(54) ***NEMESIA* PLANT NAMED 'BALARLILABI'**

(50) Latin Name: *Nemesia×hybrida*
Varietal Denomination: Balarlilabi

(75) Inventor: Paul A. Talmadge, Orcutt, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/001,168

(22) Filed: Dec. 10, 2007

(51) Int. Cl.
*A01H 5/00* (2006.01)

(52) U.S. Cl. ..... Plt./458
(58) Field of Classification Search ..... Plt./458
See application file for complete search history.

(56) References Cited

PUBLICATIONS

European Plant Breeders' Rights Application No. 2006/2146 filed Oct. 27, 206, Copy of published information from the Community Plant Office site attached.

Plant material first become available to the public Feb. 9, 2007 in the form of a European sale.

*Primary Examiner*—Kent L Bell
(74) *Attorney, Agent, or Firm*—Audrey Charles

(57) ABSTRACT

A new and distinct cultivar of *Nemesia* plant named 'Balarlilabi', characterized by its white and lavender bicolored flowers, medium green-colored foliage, and vigorous and upright growth habit.

1 Drawing Sheet

Latin name of genus and species of plant claimed: *Nemesia×hybrida.*
Variety denomination. 'Balarlilabi'.

BACKGROUND OF THE INVENTION

The present invention relates to a new and distinct cultivar of *Nemesia* plant botanically known as *Nemesia×hybrida* and hereinafter referred to by the cultivar name 'Balarlilabi'.

The new cultivar originated in a controlled breeding program in Guadalupe, Calif. during September 2003. The objective of the breeding program was the development of *Nemesia* cultivars that are freely flowering with unique flower coloration and a well-branched, compact-upright growth habit.

The new *Nemesia* cultivar is the result of cross-pollination. The female (seed) parent of the new cultivar is the proprietary *Nemesia×hybrida* breeding selection designated KJGVCCE-N, not patented, characterized by its white and lavender-bicolored flowers, medium green-colored foliage, and moderately vigorous and upright growth habit. The male (pollen) parent of the new cultivar is the proprietary *Nemesia×hybrida* breeding selection designated HHSDPOA-N, not patented, characterized by its white and lavender bicolored flowers, medium green-colored foliage, and moderately vigorous and upright growth habit. The new cultivar was discovered and selected as a single flowering plant within the progeny of the above stated cross-pollination during March 2004 in a controlled environment at Guadalupe, Calif.

Asexual reproduction of the new cultivar by terminal stem cuttings since March 2004 in a greenhouse at Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balarlilabi' as a new and distinct cultivar of *Nemesia* plant:

1. White and lavender bicolored flowers;
2. Medium green-colored foliage; and
3. Vigorous and upright growth habit.

Plants of the new cultivar differ from plants of the female and male parents primarily in growth vigor. As a result, plants of the new cultivar are taller and wider than plants of the female and male parents.

Of the many commercially available *Nemesia* cultivars, the most similar in comparison to the new cultivar is Compact Pink Innocence 'Fleuripi', U.S. Plant Pat. No. 16,851. However, in side by side comparisons, plants of the new cultivar differ from plants of 'Fleuripi' in the following characteristics:

1. Plants of the new cultivar have a flower color different from plants of 'Fleuripi'; and
2. Plants of the new cultivar are taller than plants of 'Fleuripi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balarlilabi'. Measurements and numerical values represent averages of typical plants. The plants were grown in 4.5 inch pots for 12 weeks in a greenhouse at West Chicago, Ill. Plants were pinched four weeks after transplant.

DETAILED BOTANICAL DESCRIPTION

Figure 1:
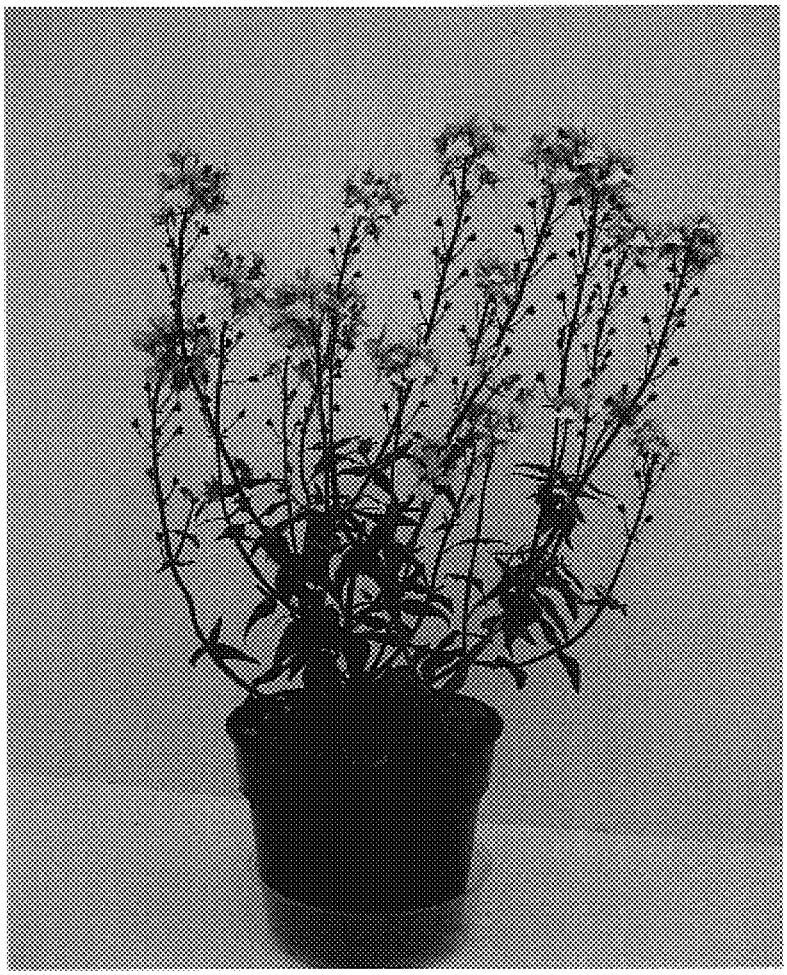
FIG. 1 illustrates a side view of the overall growth and flowering habit of 'Balarlilabi'.
Figure 2:
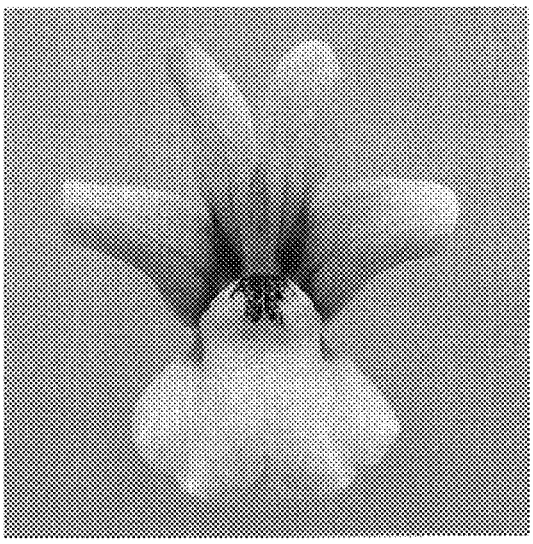
FIG. 2 illustrates a close-up view of an individual flower of 'Balarlilabi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Oct. 24, 2007 between 1:00 p.m. and 3:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. 4.5 inch pots for 12 weeks utilizing a soilless growth medium. Plants were pinched four weeks after transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Nemesia×hybrida* cultivar Balarlilabi.

Parentage:

*Female parent.*—Proprietary *Nemesia×hybrida* breeding selection designated KJGVCCE-N, not patented.

*Male parent.*—Proprietary *Nemesia×hybrida* breeding selection designated HHSDPOA-N, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fine, white in color.

*Rooting habit.*—Freely branching.

Plant description:

*Commercial crop time.*—Approximately 5 to 7 weeks from a rooted cutting to finish in a 10 cm pot.

*Growth habit and general appearance.*—Vigorous and upright.

*Size.*—Height from soil level to top of plant plane: Approximately 27.0 cm. Width: Approximately 23.3 cm.

*Branching habit.*—Freely branching. Pinching enhances lateral branching. Average quantity of branches per plant: Approximately 4 main branches with approximately 20 lateral branches.

*Lateral branch.*—Shape: Square in cross section. Strength: Moderate, flexible. Length: Approximately 20.9 cm. Diameter: Approximately 3.0 mm. Length of central internode: Approximately 2.7 cm. Texture: Glabrous. Color of young stem: 144A. Color of mature stem: 137A.

Foliage description:

*General description.*—Quantity of leaves per branch: Approximately 8.

*Fragrance.*—None. Form: Simple. Arrangement: Opposite.

*Leaves.*—Aspect: Perpendicular to obtuse angle to stem. Shape: Ovate. Margin: Widely serrate. Apex: Acute. Base: Broadly attenuate. Venation pattern: Pinnate. Length of mature leaf: Approximately 2.9 cm. Width of mature leaf: Approximately 1.3 cm. Texture of upper and lower surfaces: Glabrous. Color of upper surface of young foliage: 144A with slightly darker venation. Color of lower surface of young foliage: 144B with venation of 144A. Color of upper surface of mature foliage: 137A with slightly darker venation. Color of lower surface of mature foliage: 138A with venation of 137A.

*Petiole.*—Length: Approximately 2.0 mm. Diameter: Approximately 1.0 mm. Texture: Glabrous. Color: 137C.

Flowering description:

*Flowering habit.*—'Balarlilabi' is freely flowering under outdoor growing conditions with substantially continuous blooming from spring through autumn and year round in greenhouse environment.

*Lastingness of individual bloom.*—Approximately 4 to 6 days.

Inflorescence description:

*General description.*—Type: Terminal raceme. Flowers face upright and outwardly. Flowers not persistent. Average quantity per plant: Approximately 23. Fragrance: None. Length or height: Approximately 12.5 cm. Width: Approximately 3.5 cm. Average quantity of fully open flowers per inflorescence: Approximately 9.

*Peduncle.*—Shape: Square in cross section. Strength: Strong. Aspect: Erect. Length: Approximately 3.6 cm. Diameter: Approximately 2.0 mm. Texture: Glabrous. Color: 137A.

Flower description:

*Type.*—Solitary, zygomorphic.

*Bud.*—Rate of opening: Generally takes 2 to 3 days for bud to progress from first color to fully open flower.

*Bud just before opening.*—Shape: Ovoid with spur. Length, including spur: Approximately 1.1 cm. Diameter: Approximately 5.0 mm. Texture: Sparsely glandular pubescent. Color: 37B with spur of 144C.

*Corolla.*—Shape: Bilabiate with nectar spur. Flower has five petals; four upper petals are fused at base to form an upright lobed and arched banner lip; the fifth lower petal is modified into a larger lip with nectar spur. Width: Approximately 1.6 cm. Length: Approximately 1.9 cm. Depth: Approximately 1.1 cm.

*Upper lip.*—Shape: Oval to oblanceolate. Margin: Entire. Apex: Rounded. Length of central lobes from throat: Approximately 1.0 cm. Width of central lobes: Approximately 3.0 mm. Length of lateral lobes from throat: Approximately 7.0 mm. Width of lateral lobes: Approximately 4.0 mm. Texture of upper and lower surfaces: Glabrous. Color of upper surface when fully open: Upper and lateral lobes of 86B at base transitioning through 76B to 76D toward apex. As age, upper and lateral lobes fade to 76D with 86C at base. Color of lower surface when fully open: 76A.

*Lower lip.*—Shape: Obovate. Margin: Entire, undulate. Apex: Emarginate. Length from palate: Approximately 8.0 mm. Width: Approximately 1.0 cm. Texture of upper and lower surfaces: Glabrous. Color of upper surface when fully open: 76D. Color of lower surface when fully open: 76A. Palate length: Approximately 2.0 mm. Palate width: Approximately 2.0 mm. Palate color: 2B with glandular pubescence of 172A. Throat length: Approximately 5.0 mm. Throat width: Approximately 5.0 mm. Throat texture: Glandular pubescent. Gland color: A mixture of colorless, 2B and 172A. Throat color: 86B with a central area of 2B.

*Nectar spur.*—Length: Approximately 6.0 mm. Diameter at proximal end: Approximately 2.0 mm. Diameter at distal end: Less than 1 mm. Texture: Sparsely glandular pubescent. Color: 145D at proximal end transitioning to 76D at distal end.

*Calyx.*—Shape: Star. Diameter: Approximately 7.0 mm.

*Sepals.*—Quantity per flower: 5, fused at base. Shape: Narrow elliptic. Apex: Acute. Length: Approximately 4.0 mm. Width: Approximately 1.0 mm. Texture of upper and lower surfaces: Glandular pubescent. Color of upper and lower surfaces: 144A at base transitioning to 137A at apex.

*Pedicel.*—Strength: Strong, flexible. Aspect: At an acute angle. Length: Approximately 1.2 cm. Diameter: Less than 1.0 mm. Texture: Glandular pubescent. Color: 144A.

*Reproductive organs.*—Androecium: Stamen quantity: 4 per flower, didynamous. Filament length of longer pair: Approximately 3.0 mm. Filament length of shorter pair: Approximately 1.0 mm. Filament color: 155D, translucent. Anther shape: Bilobed, ovoid. Anther length: Less than 1 mm. Anther color: 11A. Pollen amount: Abundant. Pollen color: 11B. Gynoecium: Pistil quantity: 1 per flower. Pistil length: Approximately 2.0 mm. Stigma shape: Rounded. Stigma color: 155D, translucent. Style length: Approximately 1.0 mm. Style color: 155D, translucent. Ovary length: Approximately 1.0 mm. Ovary texture: Glabrous. Ovary color: 145A.

Seed and fruit production: Neither seed nor fruit production has been observed.

Disease and pest resistance: Resistance to pathogens and pests common to *Nemesia* has not been observed.

What is claimed is:

1. A new and distinct cultivar of *Nemesia* plant named 'Balarlilabi', substantially as herein shown and described.

* * * * *